United States Patent
Rohan et al.

(10) Patent No.: US 8,702,582 B2
(45) Date of Patent: *Apr. 22, 2014

(54) MAGNETIC FIELD TREATMENT TECHNIQUES

(71) Applicant: The McLean Hospital Corporation, Belmont, MA (US)

(72) Inventors: Michael L. Rohan, Cambridge, MA (US); Perry Renshaw, Bedford, MA (US); Aimee Parow, Phoenix, AZ (US)

(73) Assignee: McLean Hospital, Belmont, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/669,128

(22) Filed: Nov. 5, 2012

(65) Prior Publication Data

US 2013/0066138 A1    Mar. 14, 2013

Related U.S. Application Data

(63) Continuation of application No. 13/247,996, filed on Sep. 28, 2011, now Pat. No. 8,303,480, which is a continuation of application No. 11/580,272, filed on Oct. 12, 2006, now Pat. No. 8,047,979, which is a continuation-in-part of application No. 11/404,051, filed on Apr. 13, 2006, now Pat. No. 7,282,021, which is a continuation of application No. 10/452,947, filed on Jun. 2, 2003, now Pat. No. 7,033,312, which is a continuation of application No. 09/839,258, filed on Apr. 20, 2001, now Pat. No. 6,572,528.

(51) Int. Cl.
*A61N 1/00*    (2006.01)

(52) U.S. Cl.
USPC .......................................................... 600/14

(58) Field of Classification Search
USPC ....................................................... 600/9–15
See application file for complete search history.

(56) References Cited

U.S. PATENT DOCUMENTS

| | | | |
|---|---|---|---|
| 3,952,751 A | 4/1976 | Yarger | |
| 4,400,809 A | 8/1983 | Whitinger | |
| 4,428,366 A * | 1/1984 | Findl et al. ...................... | 600/14 |
| 4,993,413 A | 2/1991 | McLeod et al. | |
| 5,014,699 A | 5/1991 | Pollack et al. | |
| 5,116,304 A * | 5/1992 | Cadwell ......................... | 600/13 |
| 5,195,941 A * | 3/1993 | Erickson et al. ................ | 600/14 |
| 5,290,409 A | 3/1994 | Liboff et al. | |
| 5,441,495 A | 8/1995 | Liboff et al. | |
| 5,595,564 A * | 1/1997 | Pinna .............................. | 600/14 |
| 5,620,463 A | 4/1997 | Drolet | |

(Continued)

FOREIGN PATENT DOCUMENTS

WO    WO 98/06342    2/1998

OTHER PUBLICATIONS

"Substitute for Shock Therapy?" *Science*, 270:1409-1540 (1995).

(Continued)

*Primary Examiner* — Samuel Gilbert
(74) *Attorney, Agent, or Firm* — Fish & Richardson P.C.

(57) ABSTRACT

The invention involves enhancing brain function by stimulating the brain using magnetic fields. Applications of the new methods include improving the condition of individuals with cognitive disorders, such as depression, and studying the effects of neural stimulation using induced electric fields. These techniques can avoid deleterious effects of psychotropic pharmaceutical treatments, and provide a relatively safe, comfortable, inexpensive means of direct cranial stimulation.

15 Claims, 8 Drawing Sheets

(56) References Cited

U.S. PATENT DOCUMENTS

| | | | |
|---|---|---|---|
| 5,658,322 | A | 8/1997 | Fleming |
| 5,669,868 | A | 9/1997 | Markoll |
| 5,725,471 | A | 3/1998 | Davey et al. |
| 5,769,778 | A | 6/1998 | Abrams et al. |
| 5,813,970 | A | 9/1998 | Abrams et al. |
| 5,833,600 | A | 11/1998 | Young |
| 5,997,464 | A * | 12/1999 | Blackwell ................ 600/13 |
| 6,029,090 | A | 2/2000 | Herbst |
| 6,086,525 | A | 7/2000 | Davey et al. |
| 6,132,361 | A | 10/2000 | Epstein et al. |
| 6,155,966 | A | 12/2000 | Parker |
| 6,161,048 | A | 12/2000 | Sluijter et al. |
| 6,198,958 | B1 | 3/2001 | Ives et al. |
| 6,290,638 | B1 | 9/2001 | Canedo et al. |
| 6,366,813 | B1 | 4/2002 | DiLorenzo |
| 6,402,678 | B1 | 6/2002 | Fiscell et al. |
| 6,491,620 | B1 | 12/2002 | Davey |
| 6,572,528 | B2 | 6/2003 | Rohan et al. |
| 6,641,520 | B2 | 11/2003 | Bailey et al. |
| 6,849,040 | B2 | 2/2005 | Ruohonen et al. |
| 6,926,660 | B2 | 8/2005 | Miller |
| 7,033,312 | B2 | 4/2006 | Rohan et al. |
| 7,087,008 | B2 | 8/2006 | Fox et al. |
| 7,282,021 | B2 | 10/2007 | Rohan et al. |
| 7,483,747 | B2 | 1/2009 | Gliner et al. |
| 7,520,848 | B2 | 4/2009 | Schneider et al. |
| 7,587,230 | B2 | 9/2009 | Litovitz |
| 7,651,459 | B2 | 1/2010 | Cameron et al. |
| 7,658,704 | B2 | 2/2010 | Fox et al. |
| 7,854,232 | B2 | 12/2010 | Aho et al. |
| 7,857,746 | B2 | 12/2010 | Riehl |
| 7,976,451 | B2 | 7/2011 | Zangen et al. |
| 8,303,450 | B2 * | 11/2012 | McKinnon ................ 475/168 |
| 2003/0181791 | A1 | 9/2003 | Thomas et al. |
| 2004/0010177 | A1 | 1/2004 | Rohan et al. |
| 2005/0234286 | A1 | 10/2005 | Riehl et al. |
| 2006/0161039 | A1 | 7/2006 | Juliana et al. |
| 2007/0260107 | A1 | 11/2007 | Mishelevich et al. |
| 2008/0200749 | A1 | 8/2008 | Zheng et al. |
| 2009/0187062 | A1 | 7/2009 | Saitoh |
| 2010/0113959 | A1 | 5/2010 | Pascual-Leone et al. |
| 2011/0060179 | A1 | 3/2011 | Aho et al. |

OTHER PUBLICATIONS

Adler, C. et al., "*Abnormal frontal white matter tracts in bipolar disorder: a diffusion tensor imaging study*" Bipolar Disorders, (6):197-203, 2004.

Adler, C. et al., "*Evidence of White Matter Pathology in Bipolar Disorder Adolescents Experiencing Their First Episode of Mania: A Diffusion Tensor Imaging Study*" Am J Psychiatry, (163):322-324, 2006.

Beyer, J. et al., "*Cortical White Matter Microstructural Abnormalities in Bipolar Disorder*" Neuropsychopharmacology, (30):2225-2229, 2005.

Boroojerdi et al., "Enhancing Analogic Reasoning With rTMS Over the Left Prefrontal Cortex," *Neurology*, 56:526-528 (2001).

Carlezon Jr., W. et al, "*Antidepressant-like Effects of Cranial Stimulation Within a Low-Energy Magnetic Field in Rats*", BIOL Psychiatry 2005; 57: 571-576; 2005 Society of Biological Psychiatry.

Cohen et al., "Effects of Coil Design on Delivery of Focal Magnetic Stimulation. Technical Considerations," *Electroencephalography and Clinical Neurophysiology*, 75:350-357 (1990).

Collins, "The Field Workers," *New Scientist*, No. 2224:36-39 (Feb. 2000).

Cracco et al., "Cerebral Function Revealed by Transcranial Magnetic Stimulation," *J. Neuroscience Methods*, 86:209-219 (1999)

Data Translation UM-16150-C DT VPI™ User's Manual, Version 6.0, Third Edition, Jul. 2000, Copyright © 1997, 1998, 2000 by Data Translation, Inc. Copyright © 2000 by Agilent Technologies.

Data Translation UM-16866-C DT3010 Series User's Manual, Third Edition, Dec. 2000, Copyright © 1998, 2000 by Data Translation, Inc.

Data Translation UM-18326-C DataAcq SDK User's Manual, Third Edition, Jul. 2001, Copyright © 1998, 2000 by Data Translation, Inc.

Di Lazzaro et al., "Comparison of Descending Volleys Evoked by Transcranial Magnetic and Electric Stimulation in Conscious Humans," *Electroencephalography and Clinical Neurophysiology*, 109:397-401 (1998).

Dolberg et al., "Transcranial Magnetic Stimulation-Induced Switch Into Mania: A Report of Two Cases," *Biol. Psychiatry*, 49:468-470 (2001).

Eschweiler et al., "Left Prefrontal Activation Predicts Therapeutic Effects of Repetitive Transcranial Magnetic Stimulation (rTMS) in Major Depression," *Psychiatry Research*, Neuroimaging Section 99:161-172 (2000).

George et al., "A Controlled Trial of Daily Left Prefrontal Cortex TMS for Treating Depression," *Biol. Psychiatry*, 48:962-970 (2000).

George et al., "Transcranial Magnetic Stimulation: A Neuropsychiatric Tool for the $21^{st}$ Century," *J. Neuropsychiatry*, vol. 8, No. 4: 373-382 (1996).

Hallett, "Transcranial Magnetic Stimulation and the Human Brain," *Nature*, 406:147-150 (Jul. 2000).

Hausmann et al., "Chronic Repetitive Transcranial Magnetic Stimulation Enhances c-fos in the Parietal Cortex and Hippocampus," *Molecular Brain Research*, 76:355-362 (2000).

Hoptoman, M. et al., "*DTI and impulsivity in schizophrenia: a first voxelwise correlation analysis*" NeuroReport, (15/16):2467-2470, 2004.

HP E1340A Arbitrary Function Generator Module User's Manual, Edition 3, Copyright © 1995 Hewlett-Packard Company.

HP E1340A Arbitrary Function Generator, B-Size, Technical Specifications, Copyright © Apr. 1999, Hewlett-Packard Company, HP Publication No. 5965-5533E.

Hulshoff Pol, H. et al., "*Focal white matter density changes in schizophrenia: reduced inter-hemispheric connectivity*" NeuroImage, (21):27-35, 2004.

Kalus, P. et al., "*New evidence for involvement of the entorhinal region in schizophrenia: a combined MRI volumetric and DTI study*" NeuroImage, (24):1122-1129, 2005.

Kalus, P. et al., "*The amygdale in schizophrenia: a trimodal magnetic resonance*", Neuroscience Letters,(375):151-156, 2005.

Keck et al., "Neuroendocrine and Behavioral Effects of Repetitive Transcranial Magnetic Stimulation in a Psychopathological Animal Model Are Suggestive of Antidepressant-Like Effects," *Neuropsychopharmacology*, vol. 24, No. 4: 337-349 (2001).

Kimbrell et al., "Frequency Dependence of Antidepressant Response to Left Prefrontal Repetitive Transcranial Magnetic Stimulation (rTMS) As a Function of Baseline Cerebral Glucose Metabolism," *Biol. Psychiatry*, 46:1603-1613 (1999).

Kolbinger et al., "Transcranial Magnetic Stimulation (TMS) in the Treatment of Major Depression—A Pilot Study," *Human Psychopharmacology*, vol. 10: 305-310 (1995).

Lisanby et al., "Magnetic Seizure Therapy of Major Depression," *Arch Gen Psychiatry*, vol. 58: 303-304 (2001).

Lisanby et al., "Sham TMS: Intracerebral Measurement of the Induced Electrical Field and the Induction of Motor-Evoked Potentials," *Biol. Psychiatry*, 49: 460-463 (2001).

Loo et al., "Effects of a 2- to 4-Week Course of Repetitive Transcranial Magnetic Stimulation (rTMS) on Neuropsychologic Functioning, Electroencephalogram, and Auditory Threshold in Depressed Patients," *Biol. Psychiatry*, 49:615-623 (2001).

Lyoon, I. et al., "*Decrease in Genu of the Corpus Callosum in Medication-Naïve, Early-Onset Dysthymia and Depressive Personality Disorder*", Society of Biological Psychiatry, (52) 1134-1143, 2002.

McConnell, "The Transcranial Magnetic Stimulation Motor Threshold Depends on the Distance From Coil to Underlying Cortex: A Replication in Healthy Adults Comparing Two Methods of Assessing the Distance to Cortex," *Biol. Psychiatry*, 49:454-459 (2001).

Nakamura, M. et al., "*Fronto-Temporal Disconnectivity in Schizotypal Personality Disorder: A Diffusion Tensor Imaging Study*" Biol Psychiatry, (58):468-478, 2005.

National Instruments DAQ 6023E/6024E/6025E User Manual; Multifunction I/o Devices for PCI, PXI™, CompactPCI, and PCMCIA Bus Computers, Dec. 2000 Edition, Part No. 322072C-01, © Copyright 1998, 2000 National Instruments Corporation.

(56) References Cited

OTHER PUBLICATIONS

National Instruments, Serial, Getting Started with Your PCMCIA Serial Hardware and Software for Windows 2000, Sep. 2000 Edition, Part No. 322951A-01, © Copyright 2000 National Instruments Corporation.

Nobuhara, K. et al., "*Frontal white matter anisotropy and symptom severity of late-life depression: a magnetic resonance diffusion tensor imaging study*" J Neurol Neurosurg Phychiatry, (77):120-122, 2006.

Oh, J. et al., "*Shape changes of the corpus callosum in abstinent methamphetamine users*" Neuroscience Letters, (384):76-81, 2005.

Okugawa, G. et al., "*Subtle Disruption of the Middle Cerebellar Peduncles in Patients with Schizophrenia*" Neuropsychobiology, (50):119-123, 2004.

Pascual-Leone et al., "Rapid-Rate Transcranial Magnetic Stimulation of Left Dorsolateral Prefrontal Cortex in Drug-Resistant Depression," *The Lancet*, 348: 233-237 (Jul. 1996).

Posse, S. et al. "*High Speed 1H Spectroscopic Imaging in Human Brain by Echo Planar Spatial-Spectral Encoding*", MRM 33:34-40 (1995) From the Diagnostic Radiology Department, The Warren Grant Magnuson Clinical Center (S.P., D.L.B.), the Neuroimaging Branch, National Institute of Neurological Disorders and Stroke (G.T.) and the Section on Clinical Pharmacology, National Institute of Mental Health (R.R.), National Institutes of Health, Bethesda, Maryland and St Jude Children's Research Hospital, Memphis, Tennessee (R.O.).

Rosenbaum et al., "Vagus Nerve Stimulation for Treatment-Resistant Depression," *Biol. Psychiatry*, 47:273-275 (2000)

Roth et al., "A Theoretical Calculation of the Electric Field Induced in the Cortex During Magnetic Stimulation," *Electroencephalography and Clinical Neurophysiology*, 81:47-56 (1991).

Sackeim, "Repetitive Transcranial Magnetic Stimulation: What Are the Next Steps?," *Biol. Psychiatry*, 48:959-961 (2000).

Siegle et al., "Pupillary and Reaction Time Measures of Sustained Processing of Negative Information in Depression," *Biol. Psychiatry*, (2001).

Stehling, M. et al. "*Echo-Planar Imaging: Magnetic Resonance Imaging in a Fraction of a Second*" Science, New Series, vol. 254, No. 5028, Special Issue: Instrumentation (Oct. 4, 1991), pp. 43-50.

Stikhina et al., "Transcranial Magnetic Stimulation in Neurotic Depression," 10:26-29 (1999) (translation provided).

Szeeszko, P. et al., "*White Matter Abnormalities in Obsessive-compulsive Disorder*" Arch Gen Psychiatry, (62):782-790, 2005.

Teicher, M., "*Developmental neurobiology of childhood stress and trauma*" Psychiatric Clinics of North America, (25):397-426, 2002.

Teicher, M. "Childhood Neglect is Associated with Reduced Corpus Callosum Area" *Biol Psychiatry*, (56):80-85, 2004.

Triggs et al., "Improving Brain Function With Transcranial Magnetic Stimulation?" *Neurology*, 56:429-430 (2001).

Wassermann, "Risk and Safety of Repetitive Transcranial Magnetic Stimulation: Report and Suggested Guidelines From the International Workshop on the Safety of Repetitive Transcranial Magnetic Stimulation," *Electroencephalography and Clinical Neurophysiology*, 108:1-16 (1998).

Yehuda, R. "*The Psychiatric Clinics of North America: Recent Advances in the Study of Biological Alterations in Post-Traumatic Stress Disorder*" W.B. Sauders Company, Psychiatric clinics of North America, V. 25, No. 2, 2002.

Zyss et al., "The Behavioral and Biochemical Effects of the Magnetic Brain Stimulation and Electroconvulsive Shocks in Rats," *Psychiatria Polska*, 4:593-610 (1996).

Zyss et al., "The Magnetic Brain Stimulation in Treatment of Depression: The Search for the Perfect Stimulus," *Psychiatria Polska*, 4:611-628 (1996).

\* cited by examiner

FIG. 4

|  | N | # improved | # worse | # no change | mean BAS |
|---|---|---|---|---|---|
| Bipolar, EP-MRSI | 30 | 23 | 1 | 6 | 0.87±0.68 |
| subgroup: unmedicated | 11 | 11 | 0 | 0 | 1.18±0.41 |
| subgroup: on medication | 19 | 12 | 1 | 6 | 0.68±0.75 |
| Bipolar, sham EP-MRSI | 10 | 3 | 2 | 5 | 0.30±1.06 |
| Comparison, EP-MRSI | 14 | 4 | 0 | 10 | 0.29±0.47 |

FIG. 5

|  | Z | p |
|---|---|---|
| Bipolar, EP-MRSI vs. Bipolar, sham EP-MRSI | 2.63 | 0.009 |
| subgroups: Bipolar, EP-MRSI, unmedicated vs. Bipolar, EP-MRSI, on medication | 2.02 | 0.044 |
| Bipolar, EP-MRSI vs. Comparison, EP-MRSI | 2.61 | 0.009 |
| Comparison, EP-MRSI vs. Bipolar, sham EP-MRSI | 0.29 | 0.77 |

FIG. 11

|  | LFMS | rTMS |
|---|---|---|
| Peak magnetic field | 20 Gauss | 20,000 Gauss |
| Peak electric field | 0.75 Volt/meter | 500 Volts/meter |
| Electric field pulse shape | Monophasic pulse | Biphasic pulse |
| Electric field pulse duration | 250 microseconds | 500 microseconds |
| Electric field pulse rate | 1 kHz | 1-20 Hz |
| Electric field pulse pattern | Alternating sign | Same sign |
| Treatment duration | 20 min | 30 min |
| Electric field direction | right-to-left | circular |

MAGNETIC FIELD TREATMENT TECHNIQUES

CROSS-REFERENCE TO RELATED APPLICATIONS

This application is a continuation application of U.S. patent application Ser. No. 13/247,996, filed on Sep. 28, 2011, which is issuing as U.S. Pat. No. 8,303,480 on Nov. 6, 2011, which is a continuation application of U.S. patent application Ser. No. 11/580,272, filed Oct. 12, 2006, which is now U.S. Pat. No. 8,047,979, which is a continuation-in-part of and claims priority to U.S. patent application Ser. No. 11/404,051, filed on Apr. 13, 2006, which is now U.S. Pat. No. 7,282,021, which is a continuation application of U.S. patent application Ser. No. 10/452,947, filed on Jun. 2, 2003, which is now U.S. Pat. No. 7,033,312, which is a continuation application of U.S. patent application Ser. No. 09/839,258, filed Apr. 20, 2001, which is now U.S. Pat. No. 6,572,528. The disclosure of the prior applications are considered part of (and are incorporated by reference in) the disclosure of this application.

TECHNICAL FIELD

This invention relates to magnetic stimulation techniques, and more particularly to neural stimulation using a magnetic field.

BACKGROUND

Repetitive transcranial magnetic stimulation (rTMS) has been used with the goal of treating depression, see, e.g., George et al., *The Journal of Neuropsychiatry and Clinical Neurosciences*, 8:373, 1996; Kolbinger et al., *Human Psychopharmacology*, 10:305, 1995.

One example of an rTMS technique uses a figure-8 surface coil with loops that are 4 cm in diameter (Cadwell, Kennewick, Wash.). This coil is placed next to the scalp, and is usually positioned to direct the magnetic field at the prefrontal cortex of the brain, see, e.g., George et al., *The Journal of Neuropsychiatry and Clinical Neurosciences*, 8:373, 1996. An electric current is run through the magnetic coil to generate a magnetic field, specifically a sequence of single-cycle sinusoidal pulses where each pulse has a frequency of approximately 1800 Hz (or about 560 microseconds per pulse). These pulses are delivered at a repetition rate of 1 to 20 Hz (i.e., one pulse every 0.05 to 1 second), see, e.g., George et al, *Biological Psychiatry*, 48:962, 2000; Eschweiler et al, *Psychiatry Research: Neuroimaging Section*, 99:161, 2000.

Some subjects have declined participation in rTMS studies due to pain induced in the scalp. In addition, seizures have been reported as a result of rTMS treatment, see, George et al, *Biological Psychiatry*, 48:962, 2000; Wasserman, *Electroencephalography and Clinical Neurophysiology* 108:1, 1998.

SUMMARY

The invention concerns treating disorders using novel magnetic field techniques. These techniques have generally been termed low-field magnetic stimulation (LFMS) techniques. These magnetic field techniques generally use low field strengths, high repetition rates, and relatively uniform magnetic field gradients to improve brain function.

In one aspect of the present invention, a method of treatment involves selecting a person who experiences symptoms of a psychotic disorder, such schizophrenia or a schizoaffective disorder, and subjecting the person's head to a time-varying magnetic field which has been generated to treat the symptoms of the psychotic disorder. The magnetic field that is generated induces an electric field in air comprising a series of electric pulses, where the pulses have a duration less than about 10 milliseconds, and where each pulse has a single polarity and the pulses are separated by periods of substantially no electric field. This aspect of the invention can also be used to treat abuse or dependence on a substance such as alcohol or nicotine. In addition, it can be used to treat other disorders such as attention deficit hyperactivity disorder, post-traumatic stress disorder, obsessive-compulsive disorder, bipolar disorder, panic disorder, and pain and movement disorders.

Advantages of this aspect of the invention include the following. Subjects with disorders may benefit from the new treatment by the lessening of the severity of the condition. Treatment techniques using this method can be administered inexpensively with relative safety and comfort, and offer a substitute for or complement to treatment by medication. Applications of the new methods include improving the condition of individuals with disorders and studying the effects of brain stimulation using induced electric fields.

Embodiments of this (and other) aspects of the invention can include the following features. The duration of each pulse in the sequence can be less than or equal to about 1 millisecond. Successive electric pulses can have alternating polarity. The electric field in air can be substantially unidirectional over at least a region of the brain, such as an interior region of the brain, e.g., the prefrontal cortex. The electric field in air can be substantially spatially uniform (e.g., have a change in magnitude within 10% or 20%, or possibly larger) over at least a region of the brain, such as an interior region of the brain, e.g., the prefrontal cortex. The magnetic field that creates this electric field can be a gradient magnetic field (i.e., a magnetic field one or more of whose x, y, or z direction components varies approximately linearly in space). The effectiveness of the method of treatment can be evaluated by evaluating the person for improvement of symptoms after subjecting the person to the magnetic field.

In another aspect of the present invention, a method of treating a person who experiences symptoms of a psychotic disorder involves generating a time-varying magnetic field, where the magnetic field induces an electric field in air comprising a series of electric pulses. The series of pulses has a frequency of at least about 100 Hz, each pulse has a single polarity, and the pulses are separated by periods of substantially no electric field. Subjecting the person's head to this time-varying magnetic field treats the symptoms of the psychotic disorder, e.g., schizophrenia or a schizoaffective disorder. This aspect of the invention can also be used to treat abuse or dependence on a substance such as alcohol or nicotine. In addition, it can be used to treat other disorders such as attention deficit hyperactivity disorder, post-traumatic stress disorder, obsessive-compulsive disorder, bipolar disorder, panic disorder, and pain and movement disorders. In embodiments of this treatment protocol, the frequency of the series of electric pulses is about 1 kHz.

In another aspect of the invention, a method of treating a person who experiences symptoms of a psychotic disorder involves generating a time-varying magnetic field with a maximum strength of less than about 500 G (e.g., 50 or 225 G), where the magnetic field induces an electric field in air comprising a series of electric pulses. Each pulse has a single polarity and the pulses are separated by periods of substantially no electric field. The person's head is subjected to the time-varying magnetic field to treat the symptoms of the psychotic disorder, e.g., schizophrenia or a schizoaffective disorder. This aspect of the invention can also be used to treat abuse or dependence on a substance such as alcohol or nicotine. In addition, it can be used to treat other disorders such as attention deficit hyperactivity disorder, post-traumatic stress disorder, obsessive-compulsive disorder, bipolar disorder, panic disorder, and pain and movement disorders. In embodiments of this treatment protocol, the maximum magnetic field strength is less than about 50 G (e.g., 10 G). In other embodiments, the electric pulses have an amplitude less than about 10 V/m (e.g., 5 V/m).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4 is a table summarizing the effects of the present treatment.

FIG. 5 is a table summarizing the statistical significance of the effects of the present treatment.

FIG. 11 is a table comparing parameters for an exemplary repetitive transcranial magnetic stimulation protocol to parameters for an exemplary protocol of present magnetic field treatment methods.

DETAILED DESCRIPTION

Apparatuses and Systems

Figure 1:
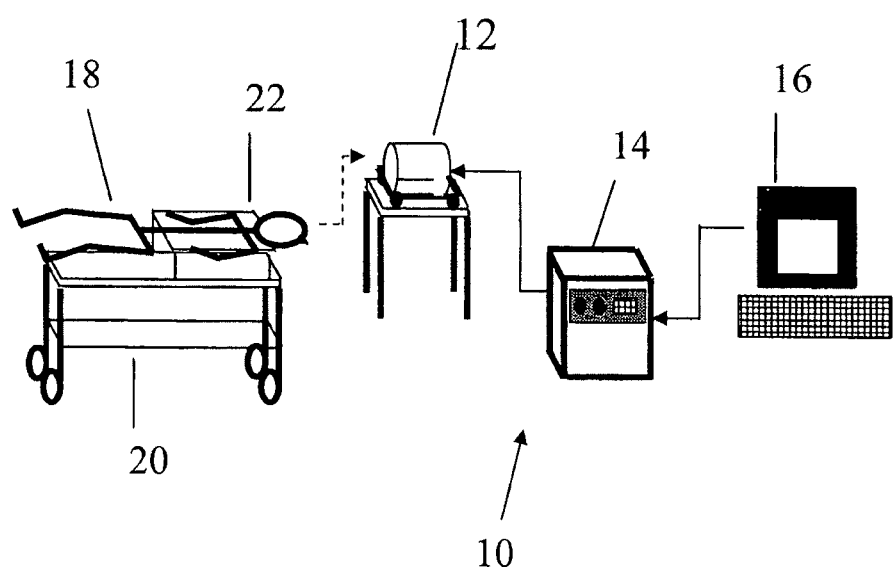
FIG. 1 is a diagram of a system and apparatus for administering the present magnetic field treatments.

A device 10 according to the present invention is shown in FIG. 1. The device 10 has a magnetic coil 12, an amplifier 14, and a waveform generator 16. The waveform generator 16 (e.g., a general-purpose programmable computer or a purpose-built electric circuit) provides an electrical pulse sequence to the amplifier 14, which amplifies the electrical signals and provides them to the magnetic coil 12.

The magnetic coil 12 produces a magnetic field in response to electrical signals received from the amplifier 14. If the signals vary in time, then it also necessarily produces an electric field, and this electric field is substantially uniform and unidirectional over the region in which the subject's brain is positioned. One way that this can be achieved is if the magnetic field has a spatial gradient that is substantially uniform (i.e. the magnetic field strength of any one vector component of the magnetic field varies substantially linearly with distance). The electric field for any coil configuration can be expressed as the sum of several potential terms; including some related to the magnetic field. If the gradient of the magnetic field is substantially uniform and unidirectional then inhomogeneity in the electric field will be reduced, providing a substantially uniform and unidirectional electric field according to Maxwell's Equations (reference Jackson 1975). (Alternatively, a magnetic coil can be used that generates a substantially uniform and unidirectional gradient magnetic field over only a region of interest of the brain, e.g., the left prefrontal cortex.) Other magnetic configurations can be utilized that are consistent with a substantially uniform electric field as required by Maxwell's Equations. The magnetic coil 12 is large enough to accommodate a subject's head, with a diameter of, e.g., about 35 cm (14 in.).

When being treated with device 10, the subject 18 lays down on a standard patient gurney 20 with a head support 22, with his or her head positioned inside the coil 12. An alternative would be to use a smaller device where only the top of the patient's head lies within the coil.

Other devices can also be used for administering the present treatment method. For instance, a conventional magnetic resonance imaging apparatus can be used. Alternatively, instead of using a device such as device 10 that consists of separate components, the device can instead integrate one or more components, e.g., to make the device easily portable. Alternatively or additionally, the magnetic coil can be included in a hat-like structure, and the waveform generator, amplifier, and power source (e.g., a battery) integrated into a control mechanism that the subject carries or wears, i.e., on his or her subject's belt. The subject can self-administer the treatment, and the treatment can be applied while the subject is lying down, standing, sitting, or in motion. Alternatively or additionally, the control device can be pre-set to administer the treatment for specific periods at specific intervals or continuously.

Methods

Prior to receiving treatment using device 10, a subject is selected as a candidate for enhancement of brain function. This selection is generally performed by medical professionals, e.g., because the subject has been diagnosed as suffering a psychiatric disorder. Alternatively, a subject could self-select based on a perceived need or desire to enhance brain function. Selection can be based on either subjective or objective criteria, including, e.g., anxiety, moodiness, depression, lethargy, sleepiness, learning difficulties, memory impairments, attention deficit hyperactivity disorder, post-traumatic stress disorder, obsessive-compulsive disorder, bipolar disorder, panic disorder, and pain and movement disorders.

To administer the treatment, the subject's head is positioned inside coil 12, and subjected to a time-varying magnetic field. (Alternatively, the subject's entire body could be positioned inside a full-body coil, and subjected to a time-varying magnetic field.)

Figure 2:
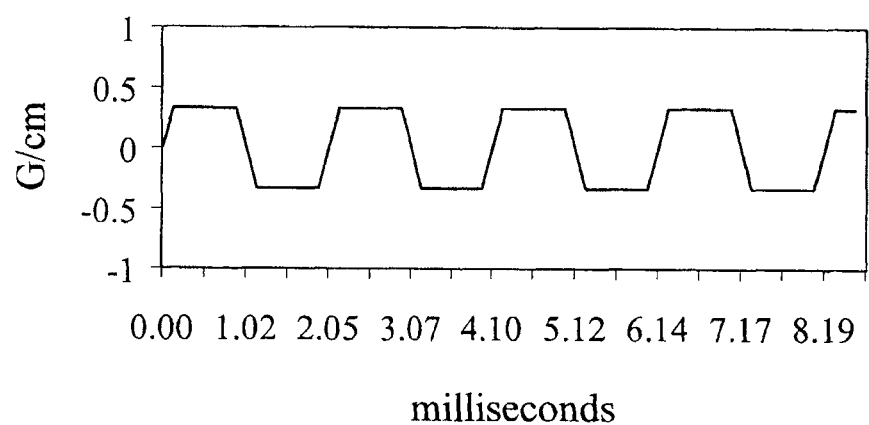
FIG. 2 is an example of a magnetic field waveform used in the present magnetic field treatment methods.

The magnetic pulse train used to generate the time-varying magnetic field is shown in FIG. 2. The pulse train comprises a sequence of pulses delivered at a high rate. As discussed in detail below, the magnetic field induces an electrical field in the subject's brain. This electrical field can interact with neurons to cause cognitive effect. In light of this, the duration of each individual magnetic pulse is selected to be on the order of the refractory period of an axon, i.e., on the order of several milliseconds, see, e.g., E. R Kandel et al., *Principles of Neural Science*, 1991, which is incorporated by reference herein. Thus, the pulse duration can be from on the order of 0.1 milliseconds to 10 milliseconds (e.g., 0.25 milliseconds).

For example, each magnetic pulse has a trapezoidal shape, with 128 microsecond ramp times (from zero to plateau) and 768 microsecond plateau times (for a total duration of 1.024 milliseconds). The pulses alternate in polarity, and may be delivered in discrete pulse trains. A single pulse train comprises 512 successive pulses, and so lasts for about a half-second. After a delay of about a second-and-a-half, the pulse train is repeated (giving one pulse train every two seconds), and the treatment concludes after about six hundred repetitions (for a total treatment time of about 20 minutes). Alternatively, the second-and-a-half delay between successive pulse trains can be eliminated.

At the plateau of each trapezoidal pulse, the maximum magnetic field strength is on the order of 5-10 G, with a magnetic field gradient of, e.g., 0.33 G/cm for some devices, 1.52 G/cm for other devices, and can be substantially greater for still other devices. Pulse sequences yielding maximum magnetic field strengths of up to about 500 G (e.g., 225 G), and maximum magnetic field gradients of up to about 25 G/cm (e.g., 13 G/cm), can alternatively be used.

These magnetic fields induce electric fields in the subject's brain. The characteristics of these electric fields are defined by the magnetic field parameters according to Maxwell's equation: $\nabla \times E(x, y, z, t) = -\partial B(x, y, z, t)/\partial t$, where $\nabla \times E$ is the curl of the electric field and $$\frac{\partial B}{\partial t}$$

is the rate of change of the magnetic field over time. In Cartesian coordinates, this equation becomes:

$\partial E_x/\partial y - \partial E_y/\partial x = -\partial B_z/\partial t$, $\partial E_y/\partial z - \partial E_z/\partial y = -\partial B_x/\partial t$, $\partial E_z/\partial x - \partial E_x/\partial z = -\partial B_y/\partial t$, where the subscripts x, y, and z denote the component of the fields along those respective axes, see, e.g., J. D. Jackson, *Classical Electrodynamics*, 1975, which is incorporated herein by reference.

These equations describe fields in free space (i.e., fields produced in the absence of other material). When conductive matter, such as brain tissue, is placed in the changing magnetic field, a charge distribution is also induced, resulting in an electric field. This electric field will affect the overall electric field in the head. This charge distribution can alter the free space electric field by up to about 50%, see Roth et al, *Electroencephalography and Clinical Neurophysiology*, 81:47, 1991, which is incorporated herein by reference. The pattern of the effect of the charge distribution will depend on the shape and placement of the subject's head.

Two local field distributions are of particular interest. In the first, the z-component (superior-inferior component) of the magnetic field has a uniform gradient in the y-direction (anterior-posterior direction), and the y-component has a uniform gradient in the z-direction: ($B_x=0$, $B_y=G(t)z$, $B_z=G(t)y$), where G(t) is the value of the gradient. In this case, the electric field can generally be described by the following equation (small additional corrective terms may be involved):

$$\left(E_x = E_0(t) + \frac{1}{2}\left(\frac{\partial G(t)}{\partial t}\right) \cdot (y^2 - z^2), E_y = 0, E_z = 0\right),$$

where $E_0(t)$ is a spatially constant field term that depends on the size of the coil and, consequently, the extent of the magnetic field. The preceding field description applies equally for the two other orientations, which are obtained by replacement of x with y, y with z, and z with x or by replacement of x with z, y with x and z with y, in both the vector components and coordinates. In addition, a given vector combination of these three field components, which forms an equivalent but rotated field, is also appropriate. Thus, one approach to applying the new treatment techniques involves using a magnetic field that has a vector component with a gradient that is substantially uniform, e.g., to within 10%, in value or direction over a relevant volume of the subject's brain, e.g., a 8 cm³ volume or the prefrontal cortex.

In another magnetic field distribution, the magnetic field is uniform over a local volume, which can be expressed as: ($B_x=0$, $B_y=0$, $B_z=B(t)$). The corresponding local electric field can generally be described by the following equation (small additional corrective terms may be involved): ($E_x=E_0(t)-a(\partial B(t)/\partial t) \cdot y$, $E_y=E_0(t)-(1-a)-(\partial B(t)/\partial t) \cdot y$, $E_z=0$), where α is an arbitrary parameter determined by the details of coil winding.

In both situations, if $E_0(t)$ is sufficiently large compared to $\partial G(t)/\partial t \cdot R^2$ or $\partial B(t)/\partial t \cdot R$, where R is an effective radius of the volume of interest, e.g., the radius of a subject's brain, then the local electric field is substantially uniform. The preceding field description applies equally for other orientations and rotations.

An LFMS magnetic field can have the following spatial dependence: $\vec{B}(x, y, z) = G(y\hat{z}+z\hat{y})$, where G is the gradient magnetic field strength in Gauss/cm (e.g., 0.33 G/cm for certain devices and 1.52 G/cm for other devices, as mentioned above) and "z hat" indicates field in the z direction. This field distribution is accurate over the region of the head but may have a different distribution outside that region.

The induced electric field accompanying the LFMS magnetic field has the following spatial dependence:

$$\vec{E}(x, y, z) = \dot{A}_0 \hat{x} + \frac{1}{2} G(y^2 + z^2)\hat{x},$$

where "$A_0$ dot" is time rate of change for the vector potential of the coil at the center of the active region and has the units of electric field (V/m) and "G dot" is time rate of change for the gradient magnetic field. "$A_0$" is a characteristic of the coil and current waveform, and determines the induced electric field strength of the coil. "$A_0$ dot" can be, e.g., 0.7 V/m for certain devices, 1.5 V/m for other devices, and substantially higher for still other devices. The electric field for the LFMS coil is substantially described by the first term, while the second term produces an inhomogeneity in the volume. The LFMS electric field waveform can be described by 5 parameters: pulse amplitude (V/m), pulse duration (μs), pulse frequency (Hz), repetition time (sec), total treatment time (min) and alternating sign of pulses (yes or no). Additionally, the electric field is characterized by a 6th parameter, the direction of the field. The preceding field description applies equally for the two other orientations, which is obtained by replacement of x with y, y with z, and z with x or by replacement of x with z, y with x and z with y, in both the vector components and coordinates. In addition, a given vector combination of these three field components, which forms an equivalent but rotated field, is also appropriate.

Figure 3:
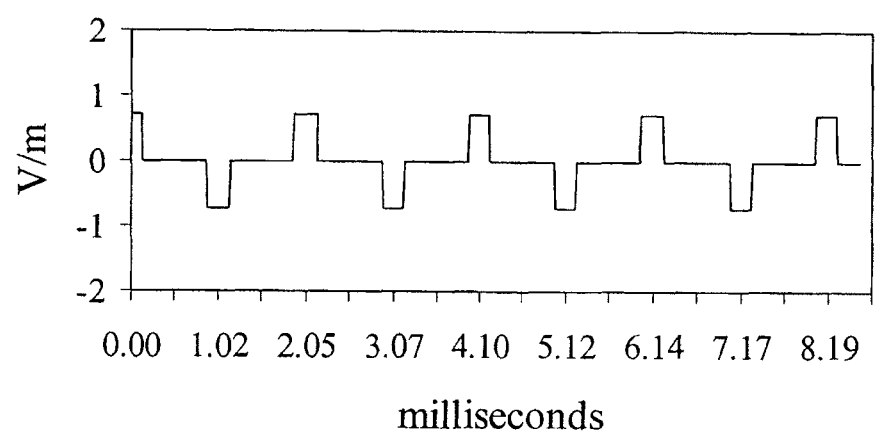
FIG. 3 is an example of an electric field waveform induced using the present magnetic field treatment methods.

FIG. 3 shows the electric field waveform induced in the subject's brain when subjected to the magnetic field waveform shown in FIG. 2. The electric field waveform is a sequence of square pulses of alternating polarity. The pulses are monophasic, here meaning that each pulse has a single polarity. Each pulse is separated from the neighboring pulses by a period of substantially no electric field. The width of each induced electric pulse corresponds to the ramping period for the magnetic field pulses, i.e., 256 microseconds. For the 1.8 G/cm magnetic field pulse amplitude, the electric field amplitude is approximately 1.4 V/m. This electric field strength is approximately an order of magnitude less than the minimum peripheral nerve stimulation threshold of approximately 6-25 V/m, see, e.g., J. P. Reilly, *Medical and Biological Engineering and Computing*, 27:101, 1989, thus providing an appropriate margin of safety against causing pain or seizures in the patient.

Use of LFMS to Affect Brain Function

The use of LFMS to date indicates that LFMS affects brain function. LFMS may affect brain function in several ways, with one mechanism being an effect on white matter tracts in the brain. White matter effects could result from an enhancement of electrophysiological function in the neurons making up the white matter tracts. White matter structures such as the corpus callosum may be especially sensitive to the LFMS electric field. This enhancement could produce results directly by increasing white matter function in diseased or compromised neurons through a mechanism similar to long-term potentiation in which neural thresholds are reduced through electrochemical changes; it could also produce results through immediate enhancement of white matter function in cortical circuits that regulate mood and affect; and both of these methods could produce longer lasting effects in post-synaptic gray matter by enhancing cell growth. It is possible that pre-synaptic interaction could provide a basis for immediate mood effects, and post-synaptic effects could provide effects associated with longer times scales such as participation in second messenger systems leading to changes in gene expression, neurotrophic responses and dendritic sprouting in the hippocampus see, E. J. Nestler et al., *Neuron* 34:13-25, 2002; M. A. Smith M A et al., *J Neurosci* 15:1768-77, 1995. In particular, post-synaptic changes could affect deficits in Brain Derived Neurotrophic Factor (BDNF) which regulates neural growth and dendtritic sprouting.

A number of disorders are associated with abnormalities in white matter tracts and BDNF deficits including mood disorders (e.g., bipolar disorder and late-life depression), psychotic disorders (e.g., schizophrenia and other schizoaffective disorders), anxiety disorders (e.g., panic disorder, OCD, and PTSD), ADHD, and substance abuse and dependence. Some of these disorders share activation deficit patterns with depression, as measured by functional magnetic resonance imaging (fMRI) and positron emission tomography (PET). LFMS may treat these disorders and alleviate their symptoms.

LFMS could affect white matter directly, enhancing white matter function. During white matter enhancement such as occurs in long term potentiation, the electric field induced during the LFMS exposure may cause the observed effects by directly affecting ion concentrations and other electrochemical signaling mechanisms within the neuron. The LFMS electric field is about 1 V/m, of a magnitude that could affect the electrochemical processes supporting neural signaling, see W. Irnich W, MAGMA 2:43-49, 1994; W. Wang et al., *In Proceedings of Joint Meeting of the Society of Magnetic Resonance Third Scientific Meeting and Exhibition and the European Society for Magnetic Resonance in Medicine and Biology*, 19-25 Aug. 1995 (pp. 73), 1995 [Nice, France: SMR/ESMRMB]. Changes in ion concentration near receptors or ion channels that are caused by the fields from LFMS could provide an effect similar to long term potentiation (LTP). This effect might be strongest in white matter tracts that particularly align with the electromagnetic field. In particular LTP has been studied for involvement in animal models of stress and depression, see M. Popoli et al., *Bipolar Disord* 4:166-82, 2002; E. Tsvetkov et al., *Neuron* 41:139-51, 2004, and has been seen in studies in animal models of depression, see Y. Levkovitz et al., *Neuropsychopharmacology* 24:608-16, 2001; M. Ogiue-Ikeda et al., *Brain Res* 993:222-6, 2003.

The direct action of LFMS on white matter could affect the function of networks of neurons in cortical areas. These effects could result from widespread interaction with neurons that participate in a "neural circuit" that controls a high order of brain function. Neural circuits have been implicated in models of depression through patterns of activation using fMRI and PET, see H. S. Mayberg, *Br Med Bull* 65:193-207, 2003.

LFMS could also enhance brain function post-synaptically by changing the function of cells located at the synapses at the termination of directly affected neurons. Post-synaptic effects include an increase in brain growth and dendritic sprouting, which reverse the degenerative effects of various diseases. The hippocampus is a brain structure that has been studied as an area that could provide a post-synaptic site for the effects of treatment. Depression, anxiety disorders, schizophrenia and substance abuse disorders are associated with neuronal degeneration in the hippocampus and reductions in dendritic branching, see R. S. Duman et al., *Arch Gen Psychiatry* 54:597-606, 1997; A. V. Kalueff et al., *Science* 312:1598-9, 2006; G. Shoval. & A. Weizman, *Eur Neuropsychopharmacol.* 15(3):319-29, 2005; P. H. Janak, *Alcohol Clin Exp Res.*, 30(2):214-21, 2006. Successful treatment of these disorders increases BDNF expression in the hippocampus, see M. Nibuya et al., *J Neurosci* 15:7539-47, 1995; B. Chen et al., *Biol Psychiatry* 50:260-5, 2001; and may increase dendritic sprouting, see S. D. Norrholm & C. C. Ouimet, *Synapse* 42:151-63, 2001; R. S. Duman et al., *Neuropsychopharmacology* 25:836-44, 2001. LFMS may additionally strengthen excitatory synaptic strength in the hippocampus through electrophysiological mecahnisms, see M. Korte et al., *J Physiol Paris* 90:157-64, 1996; H. Kang et al., *Neuron* 19:653-64, 1997. One explanation of this process suggests that reductions in neurotrophic factors, notably brain derived neurotrophic factor (BDNF), are linked to systems such as cAMP response element binding protein (CREB), through second messenger pathways such as cAMP and Ca++, see M. A. Smith et al., *J Neurosci* 15:1768-77, 1995; T. E. Meyer & J. F. Habener, *Endocr Rev* 14:269-90, 1993; A. Ghosh & M. E. Greenberg, *Science* 268:239-47, 1995. The presence of ions such as Ca in these neural signaling pathways and the electrochemical nature of many of the synaptic receptors and ion channels involved suggest that interaction of these systems with the electromagnetic fields of LFMS is possible. The timing of the LFMS waveform could be an important factor in this successful interaction. The LFMS electric field pulses are 250 microseconds in duration and delivered at 1 kHz with alternating polarity. The timing of the LFMS electric field pulses occurs on a timescale similar to the reaction times of these systems, and this may be a reason for the observation of the observed effects at such low field strengths. LFMS, with its single phase excitation pulses which have sub-millisecond duration, may interact efficiently with these signaling systems in the brain because many components of these systems (such as ion channels) have a response time on the order of 1 ms.

Antidepressant medications have been hypothesized to increase monoamines at central synapses. This, in turn, influences intracellular second messenger systems, which activates neurogenesis and dendritic sprouting in the hippocampus, and leads to improved neuronal function. It has been proposed that the antidepressant effects of magnetic stimulation of the cortex act through presynaptic inputs to the hippocampus and participate in this process, see M. Popoli M et al., *Bipolar Disord* 4:166-82, 2002. The time course of patient response to antidepressant treatments is on the order of weeks, and may be indicative of the time required for this neurogenesis, see H. K. Manji HK et al., *Biol Psychiatry* 53:707-42, 2003. This model of the antidepressant effects of magnetic stimulation of the cortex, suggesting that primary effects occur with stimulation in the cortex but have long term secondary effects in the hippocampus, may apply to LFMS.

A number of proposed mechanisms for depression have been explored using both cognitive and neurobiological models. Cognitive models have been studied with functional imaging techniques that examine metabolic and hemodynamic changes in resting brain state. These types of studies using PET and MR show a pattern of cortical hypometabolism in dorsal prefrontal cortical regions and of hypermetabolism in paralimbic and ventral cortical regions, see C. E. Bearden et al., *Bipolar Disord* 3:106-50, 2001 (in particular pages 151-53); H. S. Mayberg, *Semin Clin Neuropsychiatry* 7:255-68, 2002; R. T. Dunn et al., *Biol Psychiatry* 51:387-99, 2002; R. M. Post et al., *Ann Clin Psychiatry* 15:85-94, 2003. These metabolic states are reversed with successful treatment or remission of depression. One study identified pre-treatment perfusion levels in the rostral cingulate as a possible marker of successful treatment, see H. S. Mayberg, *Br Med Bull* 65:193-207, 2003 in manic depressive disorder, while another implicated cerebellar regions in the neurobiology of bipolar depressive disorder, see T. A. Ketter et al., *Biol Psychiatry* 49:97-109, 20001. In these models depression is discussed as a dysfunction of balanced neural circuits, with the total interaction between these areas being more important than changed function in any one area. Successful treatment or remission is accompanied by the correction of (or compensation for) this dysfunction. LFMS may interact with these networks because LFMS may induce electric fields in the axons making up these circuits, and may modify electrochemical signaling mechanisms and balance within these neural networks.

Depression has also been associated with abnormalities in white matter tracts in the brain. Abnormal white matter anisotropy within the frontal and temporal lobes has been observed in patients with late-life depression, see K. Nobuhara et al., *J Neurol Neurosurg Psychiatry* 77:120-22, 2006. A smaller genu, the region of the corpus callosum where interhemispheric fibers from the frontal regions of the brain cross, has been observed in depressed patients, see I. K. Lyoo et al., *Biol Psychiatry* 52:1134-43, 2002. In addition to general observations of abnormalities in white matter tracts in persons with depression, such abnormalities have in particular been found in persons with bipolar disorder. Microstructural changes and changes in anisotropy in white matter have been found, see C. M. Adler et al., *Bipolar Disorders*, 6:197-203, 2004; C. M. Adler et al., *Am J Psychiatry*, 163:322-24, 2006; J. L. Beyer et al., *Neuropsychopharmacology* 30:2225-29, 2005. Loss of bundle coherence in prefrontal white matter tracts or other disruption in network connectivity or white matter bundling may be implicated in the symptomatology of bipolar disorder, see Adler et al., *Bipolar Disorders*, 6:197-203, 2004. LFMS may counteract or mitigate these adverse changes, or enhance function in compromised white matter tracts by enhancing neural signaling through electrophysiological mechanisms similar to potentiation.

Schizophrenia and schizoaffective disorders have been associated with abnormalities in white matter tracts, cerebral circuit disconnectivity, hippocampal degeneration and with deficits of BDNF. Abnormalities in the amygdale, endtorhinal cortex, middle cerebellar peduncles, the genu and truncus of the corpus callosum, the internal capsule and anterior commissure of the right hemisphere, inferior frontal white matter, anterior cingulate, caudate, insula, inferior parietal lobule, left postcentral gyms, right superior/middle temporal gyms, and bilateral fusiform gyms have been observed in persons with schizophrenia, see M. J. Hoptman et al., *Brain Imaging* 15(16):2467-70, 2004; H. E. Hulshoff et al., *NeruoImage* 21:27-35, 2004; G. Okugawa, et al., *Neurophychobiology* 50:119-23, 2004; P. Kalus et al., Neuroscience Letters 375: 151-56, 2005; P. Kalus et al., *NeuroImage*, 24:1122-29, 2005; A. M. Brickman et al., *J Neuropsychiatry Clin Neurosci.,* 18(3): 364-76, 2006; and N. Rusch & G. Spalletta, *Psychiatr Danub.* 1:20, 2006. LFMS could provide treatment for the symptoms of schizophrenia and schizoaffective disorders through direct electromagnetic interaction with white matter tracts.

Schizophrenia has displayed neural circuit changes which could be part of its pathophysiology. Fronto-temporal connectivity changes in white matter tracts, such as the uncinate fasciculus and cingulum bundle, have been observed in persons with schizotypal personality disorder, see M. Nakamura et al., *Biol Psychiatry* 58:468-78, 2005, and cerebral disconnectivity has been seen in early stages of schizophrenia, see A. Federspiel et al., *Neurobiol Dis.* 22(3):702-9, 2006. Finally, schizophrenia shares some of the hippocampal volume reduction, see N. Kuroki et al., *Biol Psychiatry*, 60(1): 22-31, 2006, and BDNF dysfunction effects, see G. Shoval & A. Weizman, *Eur Neuropsychopharmacol.*, 15(3):319-29, 2005, that could benefit from any post-synaptic changes affected by LFMS treatment. Treatment of schizophrenia with rTMS has been studied with positive results, particularly in the abatement of auditory hallucinations, see P. B. Fitzgerald et al., *World J Biol Psychiatry*, 7(2):119-22, 2006; and Y. Jin et al., *Schizophr Bull.*, 32(3):556-61, 2006.

Anxiety disorders such as PTSD can benefit from post-synaptic changes affected by LFMS because they display BDNF deficits, see A. V. Kalueff et al., *Science*, 312(5780): 1598-9, 2006. PTSD and anxiety disorder have benefited from the electromagnetic rTMS treatment, see H. Cohen et al., *Am J Psychiatry*, 161(3):515-24, 2004 and may also benefit from LFMS treatment.

Drug abuse shares many of the cognitive patterns of change in regions regulating mood, cognitive function, memory and reward that are affected in depression, see N. D. Volkow et al., *Pharmacol Ther.*, 108(1):3-17, 2005. It shows changes in the hippocampus similar to those of depression, see L. Pu et al., *Nat Neurosci.*, 9(5):605-7, 2006; and P. H. Janak et al., *Alcohol Clin Exp Res.* 30(2):214-21, 2006. Treatments for drug abuse reflect this overlap with treatments for depression, and many antidepressant medications are also used in the treatment of drug abuse. LFMS could provide a treatment for drug abuse, providing beneficial effects that parallel these antidepressant based treatments.

Abnormalities in white matter tracts have also been associated with a number of other disorders, including ADHD, PTSD, and substance abuse, see Teicher et al., *Psychiatr Clin N Am* 25:397-426, 2002. For example, increased curvature in the genu of the corpus callosum and abnormalities in the posterior midbody and isthmus area of the corpus callosum have been observed in persons who abused methamphetamine, see J. S. Oh et al., *Neuroscience Letters*, 384:76-81, 2005. Evidence of abnormal white matter microstructure has also been found in patients with obsessive compulsive disorder, see *Arch Gen Psychiatry* 62:782-90, 2005. The direct action of LFMS on white matter tracts could provide treatment for these disorders.

EXAMPLES

Experiment

An experiment demonstrating the LFMS effect in the treatment of depression was performed in 2001 at McLean Hospital, see M. Rohan et al., *Am J Psychiatry*, 161(1):93-98, 2004. The study population was comprised of participants in three studies of medications for bipolar disorder. These studies were investigating the effects of conventional and non-conventional (omega3 fatty acid supplements) therapies on mood and brain chemistry over a period of time, and involved LFMS MRI scans and clinical interviews on a monthly basis. At the start of these studies the beneficial effects of LFMS were not known, and the LFMS MRI scan was an experimental MRI scan used to measure chemical concentration. Subjects had a diagnosis of Bipolar I or II Disorder and were between the ages of 18 and 65. They were either currently on a course of medication including lithium, Depakote, and other anticonvulsants, or were medication free at the start of the study. Subjects who were given anxiolytic medication during the scan sessions or who were taking medication in addition to those listed above were not considered in this study. Only mood improvement data from first visits was used to prevent confounds due to medication changes.

The "Brief Affect Scale" (BAS) measures change in immediate mood state on a 7-point scale and was administered to all subjects immediately before and after the MR scanning session. These numerically ranked responses were grouped into the ordinal categories of "improved" (3 to 1), "same" (0) and "worse" (−1 to −3) for statistical treatment.

Studies were conducted at the McLean Hospital Brain Imaging Center. Scanning was performed on a 1.5T MRI scanner. Subjects with bipolar disorder who received LFMS MRI scans received 20 minutes of LFMS sequences along with 30 minutes of anatomic MR scans at each visit. The LFMS sequence was an Echo-Planar scan that is described below. Some subjects with bipolar disorder were treated with a sham LFMS MRI scan in order to provide an experimental control. The sham MRI scan was identical to original exam, except that the LFMS sequence was replaced with a three-dimensioned spoiled gradient echo scan. Additionally, a group of healthy comparison subjects were given LFMS MRI scans with the same protocol, as a second experimental control group.

Ordered logistic regression modeling methods were used to examine the differences in BAS scores among the study groups. Data were summarized as means (±SD) or by means with 95% confidence intervals (95% CI). Two sided significance tests, requiring p<0.05 for statistical significance, were employed.

Twenty-three of 30 subjects with Bipolar Disorder reported improvement in mood of at least 1 point on the BAS scale after LFMS treatment. "No change" was reported by 6 subjects, and a worsening of mood was reported by 1 subject. The mean BAS score for bipolar subjects receiving LFMS was 0.87±0.68. In the subgroup of unmedicated bipolar LFMS subjects, 11 of 11 subjects reported improvement in mood (mean BAS score=1.18±0.41), compared to reports of improvement by 12 of 19 subjects with bipolar disorder in the subgroup taking mood stabilizing medication (mean BAS score=0.68±0.75).

Three of 10 subjects with Bipolar Disorder who received sham treatment reported improvement in mood after the exam, with 2 reports of worsening in mood. The mean BAS score for bipolar subjects receiving sham treatment was 0.30±1.06.

Four of 14 healthy subjects reported improvement in mood after an LFMS treatment, with no reports of worsening. The mean BAS score for healthy subjects receiving LFMS treatment was 0.29±0.47. Table A summarizes these BAS improvement scores.

Ordinal BAS ratings were compared between bipolar subjects who received LFMS treatment (N=30, mean BAS=0.87±0.68) vs. those receiving sham treatment (N=10, mean BAS=0.30±1.06) using ordered logistic regression methods. This difference was statistically significant (z=2.63, p=0.009). The higher BAS scores in the LFMS subjects indicate greater perceived mood improvement in this group compared to the bipolar sham LFMS group.

Ordinal BAS ratings were compared between unmedicated bipolar LFMS subjects (N=11, mean BAS improvement 1.18±0.41) and medicated bipolar LFMS subjects scans (N=19, mean BAS=0.68±0.75). This difference was statistically significant (z=2.02, p=0.044).

Ordinal BAS ratings were also compared between bipolar LFMS subjects (N=30, mean BAS=0.87±0.68) and healthy subjects who received LFMS (N=14, mean BAS=0.29±0.47). This difference was also statistically significant (z=2.61, p=0.009). The contrast between bipolar sham LFMS subjects and healthy LFMS subjects was not significant (z=0.29, p=0.77). A summary of these results is listed in FIGS. 4 and 5. FIG. 4 shows the results of the Brief Affect Scale assessment of mood in all subjects after LFMS or sham treatment. FIG. 5 shows the statistical significance of the contrast between mood improvement in the different groups of subjects.

We found significant improvement of mood in depressed subjects with bipolar disorder after LFMS treatment. This improvement was absent in bipolar subjects who received sham LFMS treatment, and was also absent in healthy subjects who received LFMS treatment. A greater effect was evident in medication-free subjects.

The treatments were administered using a General Electric 1.5T Signa MRI scanner. After optional water suppression, slice selective excitation, and a spatial phase encoding pulse, the device applied a train of 512 trapezoidal alternating-polarity magnetic field pulses. These pulses were about one millisecond long, with ramp times of 128 microseconds and 768 microsecond plateau times. During the plateau of each pulse, the gradient was 0.33 G/cm, and the maximum magnetic field in the cortex was about 5 G. The entire train of 512 pulses was repeated every 2 seconds, six hundred times, for a total treatment time of 20 minutes. FIG. 2 is a diagram of the magnetic field pulse train. The 'X' gradient coil in the magnetic resonance scanner, having an approximate diameter of about 90 cm (36 in.), was used to apply this sequence, orienting the gradient in the right-left direction for the supine subjects. The gradient of the z-component of the magnetic field from this coil in the x-direction is uniform in both magnitude and direction over a subject's brain to within about 5%.

The magnetic field induced an electric field in the brains of the subjects. This electric field was oriented from front to back, from the subject's perspective. The induced electric field consisted of 256 microsecond monophasic square pulses, where each pulse has a single polarity and an amplitude of approximately 0.7 V/m. A diagram of this electric field waveform is shown in FIG. 3.

To achieve the same electric field with a smaller coil, Maxwell's equations show that a higher magnetic field may be required. Using a coil with a similar shape but smaller diameter, e.g., a "head-sized" 35 cm (14 in.) coil instead of a 36-inch "whole-body" gradient coil that was in the MRI system, to induce a similar same electric field magnitude would employ a magnetic field that reaches approximately 50 G in the head. The magnetic field used to induce such an electric field can have a vector component with a gradient that is slightly less uniform in value and direction, varying by about 10% over the cranial volume. In addition, a higher magnetic field, e.g., 100 G, can be used with a smaller coil that provides a vector component with a substantially uniform gradient over only a region, e.g. 8 cm$^3$, of the brain.

Comparative Example rTMS employs electric fields on the order of 500 V/m in the cortex, more than sufficient to cause neural depolarization, and fields on the order of 50V/m in subcortical structures, see M. Nadeem et al., *IEEE Trans Biomed Eng,* 50:900-7, 2003. It uses a bi-phasic waveform that reverses sign during each pulse. The electric field direction for rTMS has a circular pattern similar to a projection of the magnetic loops that are its source. LFMS, however, has electric fields that are relatively weak in comparison to other stimulation techniques (<1 V/m), not enough to depolarize a neuron in general, but that penetrate uniformly through all structures. LFMS uses a monophasic waveform that does not reverse sign during the pulse. Finally, the LFMS field observed to produce this effect has a uniform direction rather than the circular direction of rTMS.

Figure 6:
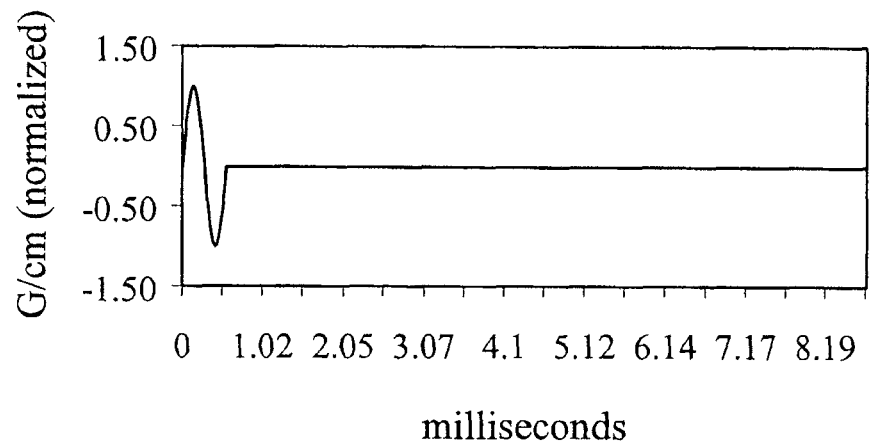
FIG. 6 is an example of a magnetic field waveform used in an example of repetitive transcranial magnetic stimulation.
Figure 8:
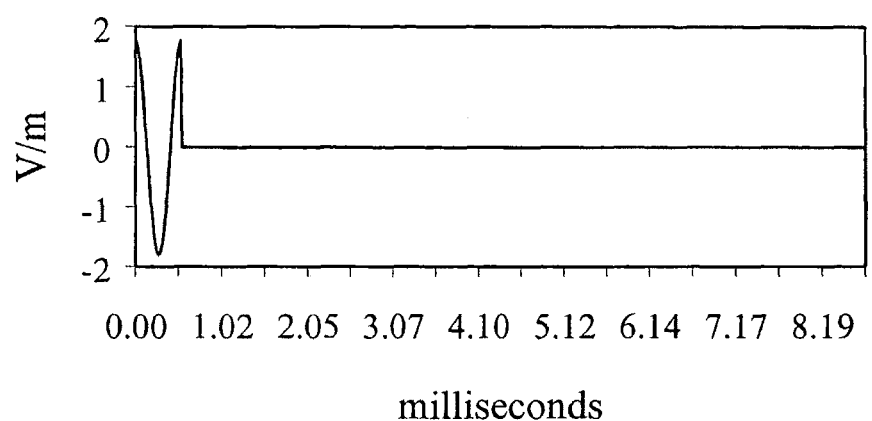
FIG. 8 is an example of an electric field waveform induced using an example of repetitive transcranial magnetic stimulation.

One example of an rTMS technique uses a figure-8 surface coil with loops that are 4 cm in diameter (Cadwell, Kennewick, Wash.). This coil is placed next to the scalp, and is usually positioned to direct the magnetic field at the prefrontal cortex of the brain, see, e.g., George et al., *The Journal of Neuropsychiatry and Clinical Neurosciences,* 8:373, 1996. An electric current is run through the magnetic coil to generate a magnetic field, specifically a sequence of single-cycle sinusoidal pulses where each pulse has a frequency of approximately 1800 Hz (or about 560 microseconds per pulse). These pulses are delivered at a repetition rate of 1 Hz (i.e., one single-cycle sinusoidal pulse every 1 second), see, e.g., George et al, *Biological Psychiatry,* 48:962, 2000; Eschweiler et al, *Psychiatry Research: Neuroimaging Section,* 99:161, 2000. This waveform is shown in FIG. 6. As the repetition period is much longer than the time span on the time axis, only one single-cycle sinusoidal pulse appears in FIG. 6.

Figure 7:
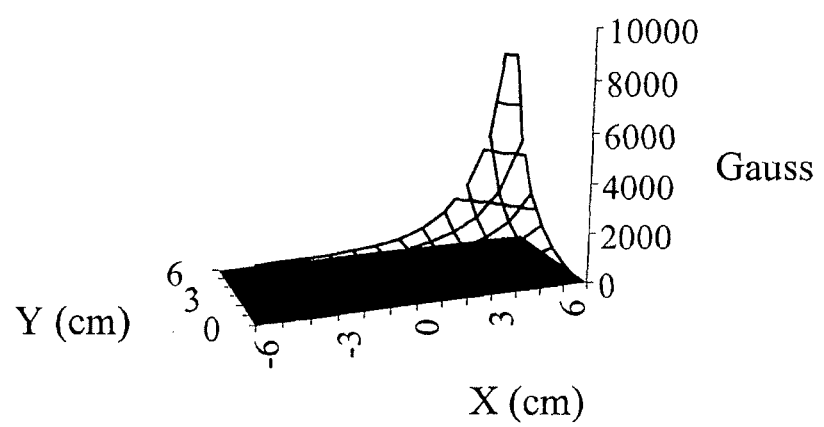
FIG. 7 is a three-dimensional plot of a magnetic field used in an example of repetitive transcranial magnetic stimulation.

The magnetic field generated by the FIG. 6 waveform is shown in FIG. 7. The field reaches its maximum strength of approximately 10,000 G at the face of the coil. The strength of this magnetic field decreases rapidly as the distance from the coil increases, to about less than 1 G at about 6 cm to 8 cm, see, e.g., Cohen et al, *Electroencephalography and Clinical Neurophysiology,* 75:350, 1990.

FIG. 8 shows the electric field waveform induced in the subject's brain by the magnetic field shown in FIG. 7. This waveform consists of a series of 560-microsecond single-cycle cosine pulses that repeat every 1 Hz.

Figure 9:
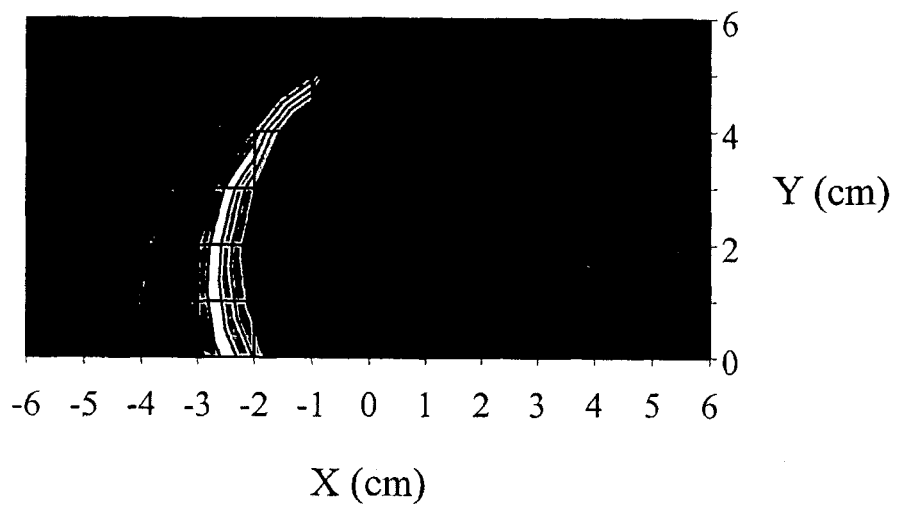
FIG. 9 is a contour plot of an electric field used in an example of repetitive transcranial magnetic stimulation.
Figure 10:
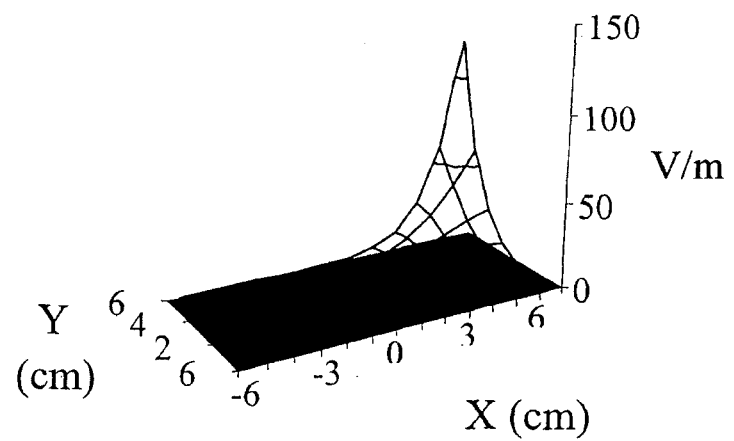
FIG. 10 is a three-dimensional plot of an electric field used in an example of repetitive transcranial magnetic stimulation.

FIG. 9 shows the contour plot and FIG. 10 shows the three-dimensional plot of the electric field induced in free space by the magnetic field shown in FIG. 2. The electric field is approximately 120 V/m at the face of the coil, and falls to about 0.02 V/m on the side of the head opposite the coil. The contours of this rapidly diminishing electric field reflect the shape of the figure-8 surface coil with 4 cm diameter loops, tilted at 45°, and placed 6.7 cm vertically and horizontally from a position equivalent to the center of the head: the electric field forms roughly circular loops.

FIG. 11 shows a table comparing parameters for an exemplary rTMS protocol to parameters for an exemplary LFMS protocol. As shown, LFMS uses a lower peak magnetic, a lower peak electric field, a lower electric field pulse duration than rTMS, and a higher field pulse rate. This LFMS technique also uses monophasic pulses of alternating sign compared to the use of biphasic pulses of the same sign in rTMS. The electric field direction in the LFMS technique is unidirectional, while the electric field direction in rTMS is circular.

A number of embodiments of the invention have been described. Nevertheless, it will be understood that various modifications may be made without departing from the spirit and scope of the invention. Accordingly, other embodiments are within the scope of the following claims.

What is claimed is:

1. A system for subjecting the head of a user to a magnetic field, comprising:
a hat-like structure comprising a magnetic coil, the hat-like structure adapted to receive the head of the user; and
a power source adapted to supply power to the magnetic coil, the power source adapted to be carried by the user
wherein the magnetic coil produces a time-varying magnetic field that induces an electric field in air comprising a series of electric field pulses, the electric field pulses being monophasic, and consecutive electric pulses being separated by non-zero duration periods of substantially no electric field.

2. The system of claim 1, wherein the power source is worn by the user.

3. The system of claim 2, wherein the power source is integrated into a belt worn by the user.

4. The system of claim 1, further comprising a waveform generator.

5. The system of claim 4, further comprising an amplifier.

6. The system of claim 5, wherein the waveform generator, amplifier and power source are integrated into a control mechanism.

7. The system of claim 6, wherein the control mechanism is worn by the user.

8. The system of claim 1 wherein the time-varying magnetic field has a maximum strength of less than 50 G.

9. The system of claim 1, wherein the power source is programmed to supply power to the magnetic coil for predetermined periods of time.

10. The system of claim 9, wherein the power source is programmed to supply power to the magnetic coil at predetermined time intervals.

11. The system of claim 9, wherein the power source is programmed to supply power to the magnetic coil continuously.

12. A system for subjecting the head of a user to a magnetic field, comprising:
a hat-like structure comprising a magnetic coil, the hat-like structure adapted to receive the head of the user;

a power source adapted to supply power to the magnetic coil, the power source adapted to be carried by the user; and a control mechanism comprising:
  a waveform generator, and
  an amplifier
wherein the magnetic coil produces a time-varying magnetic field that induces an electric field in air comprising a series of electric field pulses, the electric field pulses being monophasic, and consecutive electric pulses being separated by non-zero duration periods of substantially no electric field.

13. The system of claim 12, wherein the control mechanism is worn by the user.

14. The system of claim 12, wherein the time-varying magnetic field has a maximum strength of less than 50 G.

15. The system of claim 14, wherein the power source is programmed to supply power to the magnetic coil at predetermined time intervals.

* * * * *